US008666236B2

(12) United States Patent
Miguens et al.

(10) Patent No.: US 8,666,236 B2
(45) Date of Patent: Mar. 4, 2014

(54) HEATER ASSEMBLY FOR VOLATILE LIQUID DISPENSER

(75) Inventors: Joao Paulo Possidonio Miguens, Vendas de Azeitao (PT); Zhang Wei, Zhongshan (CN); Ren Jianhui, Zhongshan (CN)

(73) Assignee: S.C. Johnson & Son, Inc., Racine, WI (US)

( * ) Notice: Subject to any disclaimer, the term of this patent is extended or adjusted under 35 U.S.C. 154(b) by 631 days.

(21) Appl. No.: 12/972,572

(22) Filed: Dec. 20, 2010

(65) Prior Publication Data
US 2012/0153040 A1   Jun. 21, 2012

(51) Int. Cl.
*F24F 6/08* (2006.01)
(52) U.S. Cl.
USPC .................. 392/395; 392/386; 392/394
(58) Field of Classification Search
None
See application file for complete search history.

(56) References Cited

U.S. PATENT DOCUMENTS

| | | | |
|---|---|---|---|
| 4,874,924 A | 10/1989 | Yamamoto et al. | |
| 5,222,186 A | 6/1993 | Schimanski et al. | |
| 5,940,577 A | 8/1999 | Steinel | |
| 6,411,776 B1 | 6/2002 | Millan | |
| 2004/0151747 A1 | 8/2004 | Davis et al. | |
| 2009/0196586 A1 | 8/2009 | Hasik et al. | |

FOREIGN PATENT DOCUMENTS

| | | |
|---|---|---|
| CN | 2281074 | 5/1998 |
| EP | 0290159 A2 | 11/1988 |
| EP | 1372161 A1 | 12/2003 |
| WO | 2009099534 A2 | 8/2009 |

OTHER PUBLICATIONS

PCT/US2011/064552 International Search Report dated Feb. 28, 2012.
Engineering drawing in exploded perspective view of a prior art All-Out heater.

*Primary Examiner* — Thor Campbell

(57) ABSTRACT

Disclosed herein are more energy efficient heaters for dispensing volatile air treatment chemicals. The heaters have a housing with a base and a cover, the base and cover together defining an enclosure with an internal generally ring-shaped cavity and an axial through bore. One of the base and cover has an essentially cylindrical extension that is integral therewith, extends towards the other of the base and cover, and forms a portion of the axial through bore. First and second electrical contacts are positioned in the cavity with portions overlapping against a heater. A metallic heat transfer sleeve formed separately from the base and cover is positioned radially outward and around the essentially cylindrical extension, and has a flange abutting one of the contacts. Also disclosed are dispensers that incorporate these heaters.

9 Claims, 4 Drawing Sheets

HEATER ASSEMBLY FOR VOLATILE LIQUID DISPENSER

CROSS-REFERENCE TO RELATED APPLICATIONS

Not applicable.

STATEMENT REGARDING FEDERALLY SPONSORED RESEARCH/DEVELOPMENT

Not applicable

BACKGROUND OF THE INVENTION

The present invention relates to heaters used to dispense air treatment chemicals, such as insect control agents, fragrances and deodorizers. More particularly, it relates to structures incorporated into such heaters for more efficiently spreading the heat generated by a heating element to a dispensing wick.

One known type of air treatment chemical dispenser is that disclosed in U.S. patent application publication 2009/0196586, the disclosure of which is incorporated by reference. In this dispenser a liquid air treatment chemical is stored in a bottle. A wick extends into the liquid, and then projects upward out of the bottle. The upward end of the wick is surrounded by a ring-type electrical heater. Heating of a ring causes air treatment chemical to be driven from the wick to the surrounding environment.

In this 2009/0196586 device the heat is generated by a positive temperature coefficient heating element in the form of a pill-shaped tablet formed from pressed conductive granular material. Its resistivity to electrical charge generates heat, and that resistivity decreases with an increase in temperature, thereby providing an inherent desirable control function against overheating.

This product had a two-part outer housing for the heater. When assembled they formed an enclosure that was generally doughnut shaped, but hollow. There were two generally arc-shaped electrical contacts positioned in the housing to extend around a central axial through bore, the bore being sized to receive the wick. One end of one contact connected to one prong of an external plug. At the other end of that contact there was a platform designed to contact a positive temperature coefficient type pill heating element.

On the other side of the heater was placed a second arc-shaped electrical contact that also extended around the through bore. It had a connection to another plug prong at one end, and another surface at an opposed end designed to rest against an opposed side of the positive temperature coefficient pill. A spring was included to help the contacts stay in close abutment with the heater even when thermal expansion of the assembly occurred during use.

Electrical charge passed through the contacts to the heater pill, causing the pill to generate heat. The generated heat was then carried back along the contact to spread the heat around the through bore, and then to the wick. Heating of the wick facilitated volatilization of air treatment chemicals drawn up by the wick.

There was also a cylindrical extension from one outer housing part. It was surrounded by axial arc extensions integral with the electrical contacts. While these arc extensions helped improve thermal heat transfer to the wick somewhat, they added complexity and cost to the manufacture of the contacts, required some compromises in the design of the contacts, and in any event did not fully optimize energy use.

U.S. Pat. No. 6,411,776 disclosed another heater where upstanding portions of the contacts surrounded a cylindrical extension from an outer housing. While integrated axial extensions on electrodes completely surrounded the cylindrical extension from the outer housing in this device, there were still similar problems in using this type of construction (e.g. complexity; cost; material compromises; energy inefficiency).

See also U.S. Pat. No. 5,940,577 where contact elements were provided with integrated cylindrical extensions.

U.S. Pat. No. 4,874,924 disclosed another heating device where an outer housing was provided with a cylindrical extension passing through the electrical contacts. However, here an internal sleeve was positioned radially inward of the cylindrical extension. Again, in this device there were significant heat transfer inefficiencies. Further, having the sleeve partially exposed outside the housing presented other concerns.

See also CN 2281074 for an approach analogous to that used in U.S. Pat. No. 4,874,924. Similarly, there is a commercially available All-out heater of this type.

Hence, a need still exists for improved heaters for use with wick-type volatile liquid dispensers.

BRIEF SUMMARY OF THE INVENTION

The present invention provides a heater designed for use with an air treatment chemical dispenser. The heater includes a housing having a base and a cover which together define an enclosure with an internal generally ring-shaped cavity and an axial through bore. At least one of the base and cover has an essentially cylindrical extension that is integral therewith, extends towards the other of the base and cover, and forms a portion of the axial through bore.

There are also first and second electrical contacts (e.g. arc or ring shaped) positioned in the cavity, and having overlapping portions that sandwich a heating element. There is also a metallic sleeve formed separately from the base and cover and positioned radially outward around the essentially cylindrical extension.

The metallic sleeve abuts against one of the electrical contacts, preferably at least partially via a radially outwardly projecting flange formed adjacent to an end of the sleeve. There also preferably is a biasing member to facilitate holding the overlapping portions of the contacts against the heating element, notwithstanding thermal expansion of the assembly during use.

Most preferably the first and second electrical contacts and the metallic sleeve are all made of aluminum (which conducts heat very efficiently), and the cover and base are made of a heat resistant plastic such as nylon. An axially extending portion of the metallic sleeve preferably has a thickness of between 0.2 mm and 0.5 mm, and at least one of the electrical contacts preferably has a thickness adjacent the metallic sleeve of at least 0.7 mm. Making the contacts thicker than the sleeve allows them to have desired rigidity, while permitting the sleeve to be formed more easily.

The first and second electrical contacts both have their own crimping terminal for linking to power supply wiring, and the heating element is preferably a positive temperature coefficient pill-shaped heating element.

Another form the invention provides a dispenser suitable to dispense liquid volatile air treatment chemical. There is a reservoir container containing the volatile air treatment chemical and having a wick extending into the chemical and also externally of the container. There is also a support housing removably mounting the reservoir thereto, and also mounting the above type of heater therein (such that the wick extends into the heater).

Heaters of the present invention have markedly improved energy efficiency. The metallic sleeve more efficiently transfers the heat to the wick, while providing easier manufacturability as compared to structures which form parts of the electrical contacts themselves into sleeves. This is achieved without causing short circuits or other significant disadvantages.

The foregoing and other advantages of the present invention will be apparent from the following description. In the description that follows reference is made to the accompanying drawings which form a part thereof, and in which there is shown by way of illustration, and not limitation, a preferred embodiment of the invention. As this embodiment is merely illustrative it is not intended to represent the full scope of the invention. Thus, reference should therefore be made to the claims herein for interpreting the scope of the invention.

DETAILED DESCRIPTION OF THE INVENTION

Figure 1:
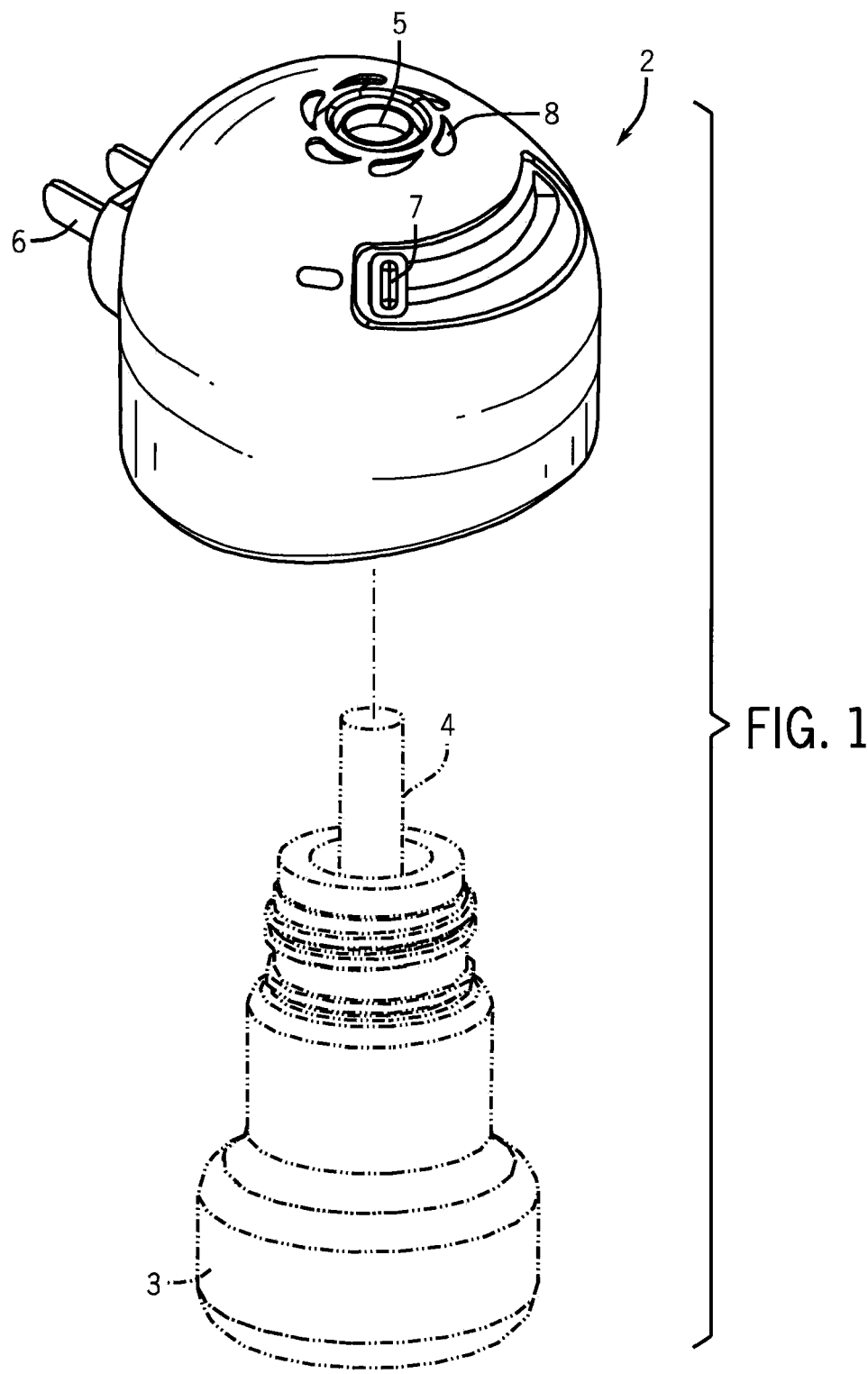
FIG. 1 depicts a volatile dispenser of the present invention adjacent a reservoir of active and an associated wick.
Figure 2:
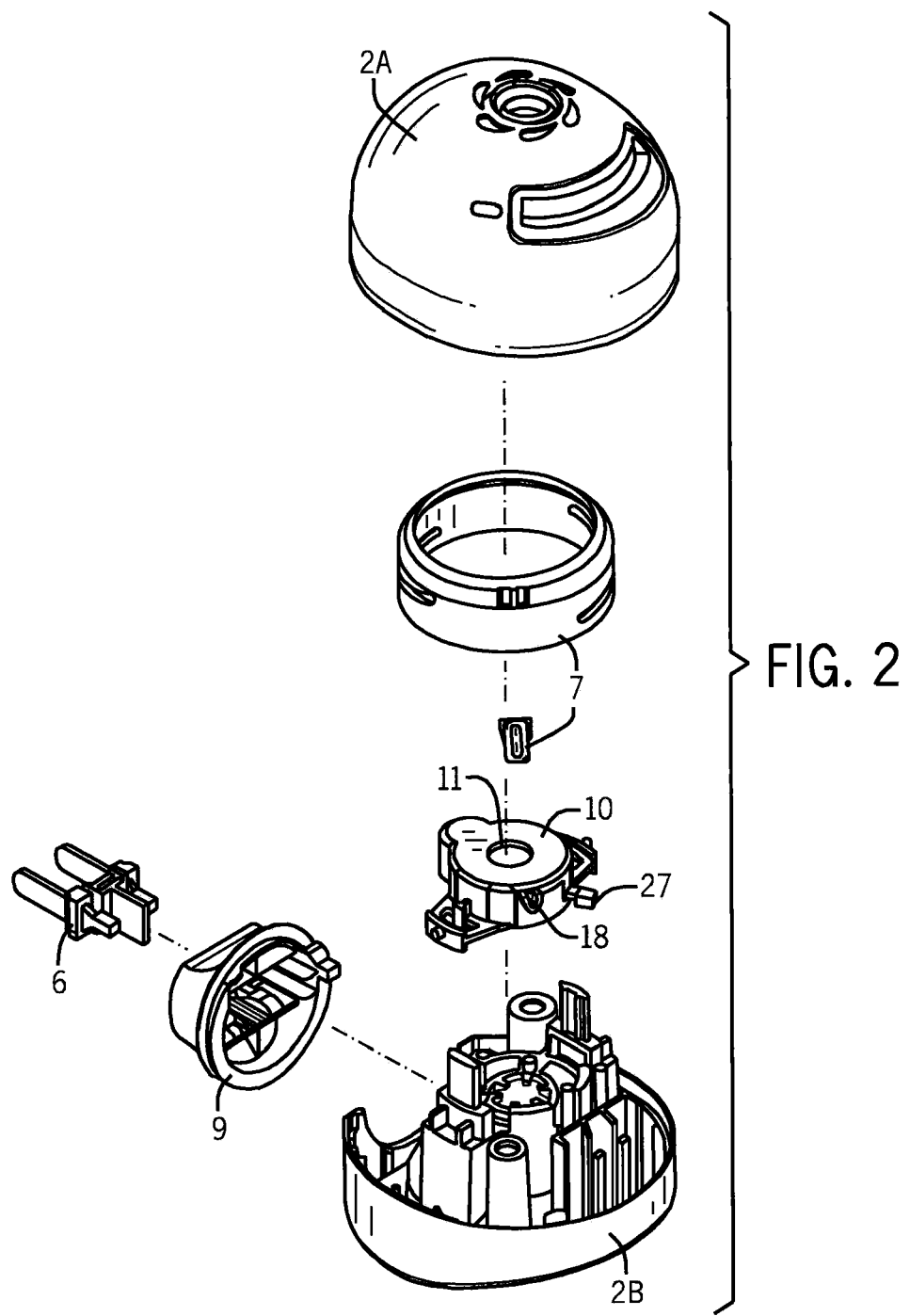
FIG. 2 is an exploded perspective view of the FIG. 1 volatile dispenser (without the reservoir and wick structures)

Turning first to FIGS. 1 and 2 there is shown an electrical dispenser 2 that is suitable to dispense a volatile air treatment chemical from a replaceable or refillable reservoir 3. The reservoir contains an air treatment chemical dissolved in a solvent (e.g. transfluthrin repellent in a hydrocarbon solvent), with a wick 4 extending down into the liquid and also externally upwardly there from. The reservoir 3 can be threadedly mounted to lower part 2B of the dispenser such that the wick extends axially into the dispenser 2 via bore 5.

There are electrical plugs 6 to supply power, as well as an adjuster ring/button assembly 7. Vent holes 8 allow air treatment chemical fumes driven from the wick to be vented to the environment.

Top housing portion 2A assembles with the lower housing portion 2B. Inside a cavity formed thereby is positioned a plug deck 9 for mounting the plugs 6 to the lower housing 2B.

There is also heater unit 10 of the present invention. It has an axial through bore 11 that can be aligned in the dispenser 2 so that the wick 4 can be inserted therein as well. When the dispenser 2 is plugged into a room outlet power will be provided to the heater 10, which in turn will generate heat that passes to the wick 4. This drives volatile off the wick and ultimately through vent holes 8.

Figure 3:
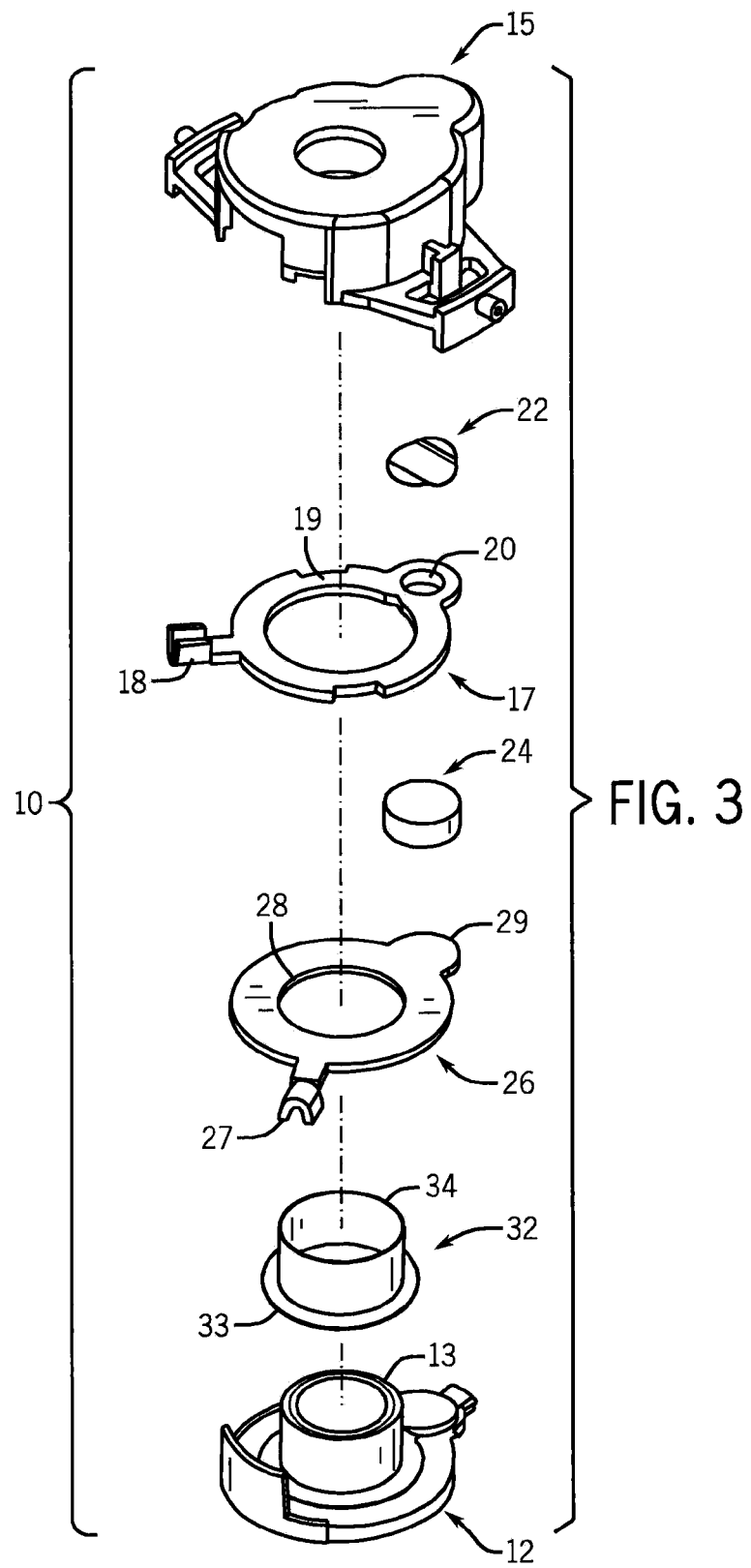
FIG. 3 is an exploded perspective view of the heater depicted in FIG. 2.

Turning now to FIG. 3, heater 10 is depicted in exploded view. It has a base 12 that has an extension 13 that is generally cylindrical and integral therewith. There is also an upper cover 15. Together the base 12 and upper cover 15 form a heater enclosure.

There are also generally ring-shaped electrical contacts 17 and 26. These are preferably made from a material that is both highly heat conductive and electrically conductive, such as aluminum. It is desirable that the contacts be at least 0.7 mm in thickness (e.g. 1 mm) so as to provide adequate rigidity to contact the heater pill 24 over prolonged periods in an effective manner. However, attempting to bend portions of such thicker contacts themselves into heat transfer axial sleeve configurations complicates manufacturability and adds cost.

Upper contact 17 has a crimping terminal 18, a through bore 19, and a platform 20. The lower contact 26 has its own crimping terminal 27, through bore 28, and platform 29.

When the heater 10 is assembled as in FIG. 2 the crimping terminals 18 and 27 project out from the heater enclosure, so as to be able to link to wires (not shown) connected to the plugs 6.

Platforms 20 and 29 are positioned to overlap each other and sandwich a positive temperature coefficient pill type heater. There is also a spring member 22 to help bias the contacts firmly against the heater.

A heat transfer metallic sleeve 32 has a radially extending lower flange 33 and an axial cylindrical sleeve 34. It is preferred that the sleeve 32 be formed with a thickness of between 0.3 mm and 0.5 mm. This thinness allows easy workability to form the piece, while still permitting excellent thermal conduction.

Figure 4:
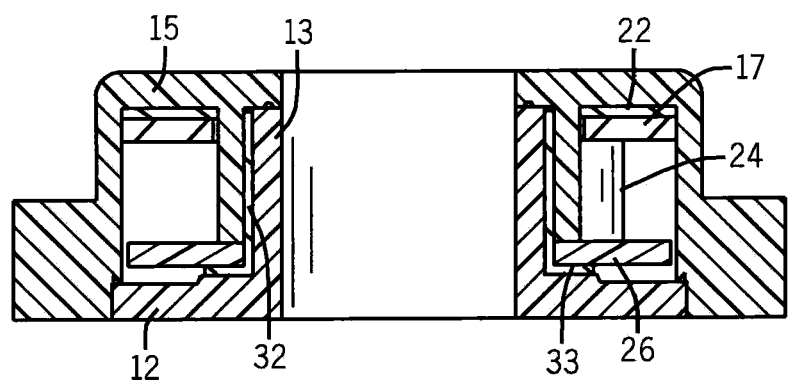
FIG. 4 is a sectional view taken through the FIG. 3 heater when the FIG. 3 heater has been assembled.

The sleeve 32 is press fit onto the extension 13 of the lower housing 12. Flange 33 is designed to abut the lower contact 26 (as best seen in FIG. 4). This allows the sleeve 32 to even more efficiently transmit heat.

Surprisingly, in tests heater 10 provided more than two times the energy efficiency of a benchmark All-out commercial heater. Using the present invention more dispensing can therefore take place for a given energy use setting, or alternatively the power usage can be reduced while still achieving the same level of dispensing.

Heating element 24 may be any conventional heating device (e.g. especially various types of resistance heaters). However, a highly preferred heating element is the pill-shaped positive temperature coefficient device 24 previously discussed. It is most preferably comprised of resistive material, for example, a ceramic, formed into a pill-shape with a film of conductive material applied to the top and bottom surface of the resistive material.

Separate domed spring 22 may also be provided to correct for thermal expansion during use. However, if desired, it need not be included, or other forms of biasing members may be used.

While a preferred embodiment of the present invention has been described above, it should be appreciated that there are still other embodiments of the invention within the spirit and scope of this disclosure. For example, the electrical contacts need not include full rings as shown, but rather may be partial arc segments as depicted in U.S. patent application publication 2009/0196586. Also, the extension 13 need not be formed only from the lower base. Rather, it may be part of the upper cover 15 instead, or be formed partially from both the lower base 12 and upper cover 15. Hence, the invention is not to be limited to just the specific embodiment shown and described.

INDUSTRIAL APPLICABILITY

The invention provides energy efficient heaters for use with a dispenser of volatile air treatment chemicals, as well as dispensers using those heaters.

What is claimed is:

1. A heater suitable for use with an air treatment chemical dispenser, the heater comprising:
   a housing having a base and a cover, the base and cover together defining an enclosure with an internal generally ring-shaped cavity and an axial through bore, wherein at least one of the base and cover has an essentially cylindrical extension that is integral therewith, extends towards the other of the base and cover, and forms a portion of the axial through bore;

a first electrical contact positioned in the cavity;

a second electrical contact also positioned in the cavity and having a portion overlapping the first electrical contact;

a heating element sandwiched between the first and second electrical contacts at a position where the first and second electrical contacts overlap; and a metallic sleeve formed separately from both of the electric contacts, the base and the cover, and positioned radially outward and around the essentially cylindrical extension.

2. The heater of claim 1, wherein the metallic sleeve abuts only one of the electrical contacts.

3. The heater of claim 2, wherein the metallic sleeve is formed with a radially outwardly projecting flange adjacent an end thereof, and the projecting flange abuts one of the electrical contacts.

4. The heater of claim 1, further comprising a spring to facilitate holding overlapping portions of the contacts against the heating element.

5. The heater of claim 1, wherein the first and second electrical contacts and the metallic sleeve are made of aluminum, and the cover and base are made of plastic.

6. The heater of claim 1, wherein an axially extending portion of the metallic sleeve has a thickness of between 0.2 mm and 0.5 mm, and at least one of the electrical contacts has a portion which has a thickness of at least 0.7 mm.

7. The heater of claim 1, wherein both of the first and second electrical contacts have their own crimping terminal.

8. The heater of claim 1, wherein the heating element is a positive temperature coefficient pill-shaped heating element.

9. A dispenser suitable to dispense liquid volatile air treatment chemical, comprising:

a reservoir container containing the volatile air treatment chemical and having a wick extending into the chemical and also externally of the container; and a support having a means for removably mounting the reservoir thereto and also means for mounting the heater of claim 1 therein such that the wick extends into the heater.

* * * * *